United States Patent
Wagenknecht et al.

[11] Patent Number: 5,565,039
[45] Date of Patent: Oct. 15, 1996

[54] METHOD FOR DISSOLUTION OF SOFT METALS FROM A SUBSTRATE OF A HARDER METAL

[76] Inventors: John H. Wagenknecht, 7510 Horseplay La., Cedar Hill, Mo. 63016; Gary V. Johnson, 4 Westford Ct., St. Charles, Mo. 63304

[21] Appl. No.: 513,660

[22] Filed: Aug. 11, 1995

Related U.S. Application Data

[63] Continuation of Ser. No. 253,667, Jun. 3, 1994, abandoned.

[51] Int. Cl.⁶ .............. B08B 3/08; C23G 1/00; C23G 1/02; C23G 5/036
[52] U.S. Cl. .............. 134/2; 134/3; 134/41; 134/28; 134/22.14; 134/22.19; 252/79.1
[58] Field of Search .......... 134/2, 3, 41, 22.14, 134/22.19, 28; 252/544

[56] References Cited

U.S. PATENT DOCUMENTS

| | | | |
|---|---|---|---|
| 3,667,949 | 7/1972 | Brindisi, Jr. et al. | 252/79.4 |
| 3,853,618 | 12/1974 | Smith | 134/3 |
| 4,004,956 | 1/1977 | Brindisi, Jr. | 252/79.4 |
| 4,397,753 | 8/1983 | Czaja | 252/79.3 |
| 4,439,338 | 3/1984 | Tomaiuolo et al. | 252/79.1 |
| 4,687,545 | 8/1987 | Williams et al. | 156/651 |
| 5,030,427 | 7/1991 | Monzyk | 423/112 |
| 5,035,749 | 7/1991 | Haruta et al. | 134/2 |

OTHER PUBLICATIONS

Fritz et al. (1981), The Reduction of $CBr_2 F_2$ by Lead—a Novel Pathway to Difluorocarbene, *Z. Naturforsch* 36b:1375–1380.

Kokkinidis et al. (1981), The Electrocatalytic Influence of Underpotential Lead Adsorbates on the Reduction of Nitrobenzene and Nitrosobenzene on Silver Single Crystal Surfaces in Methanolic Solutions, *Electrochimica Acta* 26:971–977.

Udupa et al. (1976), Electrosynthesis of Organic Compounds Employing Dissolving Type of Cathodes, *Transaction of the SAEST* 11:153–157.

Azoo et al. (1968), Lead as a Reducing Agent in the Preparation of Bibenzyls and Aromatic Aoxy–Compounds, *J. Chem. Soc. C*:2403–2405.

*Primary Examiner*—Zeinab El-Arini
*Attorney, Agent, or Firm*—Howell & Haferkamp, L.C.

[57] ABSTRACT

A method for selectively dissolving a soft metal from a substrate of a harder metal by application thereto of an organic nitrocompound and a carboxylic acid. The organic nitrocompound, upon exposure to the soft metal, oxidizes the soft metal to form a first soft metal salt. The carboxylic acid, upon exposure to the soft metal salt, reacts with the first soft metal salt to form a second soft metal salt that is soluble in the composition.

28 Claims, No Drawings

METHOD FOR DISSOLUTION OF SOFT METALS FROM A SUBSTRATE OF A HARDER METAL

This is a continuation of application Ser. No. 08/253,667 filed on Jun. 3, 1994, now abandoned.

BACKGROUND OF THE INVENTION

1. Field of the Invention

The present invention relates to solvents for soft metals such as lead, copper and related alloys, and more particularly to mixtures that dissolve such metals selectively, permitting removal of such metals from surfaces of steel, nickel and the like.

2. Description of the Prior Art

Often, undesirable deposits of soft metals, such as lead, copper, cadmium, tin, alloys thereof (e.g., solder, a lead-tin alloy) and the like, accumulate on harder metal surfaces such as surfaces of steel, stainless steel, nickel and the like. For example, as bullets or shot pass through the steel barrel of a rifle or other gun, they leave deposits of lead on the bore or interior surface of the barrel. After time and repeated firing of the gun, the deposits accumulate, developing into an increasingly thicker coating of lead on the interior surface of the barrel and leading to decreased shooting accuracy. For bullets jacketed in copper, copper coatings develop on the interior surface of the barrel by the same process. It is therefore necessary to clean the barrel occasionally to remove such coatings.

Other examples of instances in which soft metals must be removed from harder metal substrates include the polishing of brass and the cleaning of soldering surfaces from extraneous solder. With respect to the latter instance, under current practices automobile starters and generators are often burned to melt solder connections to allow recovery of the copper parts for salvage.

A variety of mixtures for dissolving lead and other soft metals are available commercially and have been described in various articles. Solvents for cleaning lead from the barrels of guns are provided by a number of suppliers. Examples of such solvents include Accubore bore cleaner of RTI Research Ltd., Vancouver, British Columbia, Canada, Shiloh Creek bore solvent of Shiloh Creek, Cottleville, Miss., Sweets 7.62 Solvent of L. Sweet, Kingsford, N.S.W., Australia, Proshot Copper Solvent II of Pro-Shot Products, Taylorville Ill., Hoppe's Bench Rest Copper Solvent of Penguin Industries, Inc., Coatesville, Pa., and Shooter's Choice Firearms Bore Cleaner of VENCO Industries, Inc., Chagrin Falls, Ohio.

However, conventional lead solvents typically suffer from a number of drawbacks. For instance, conventional products generally are not as selective as desired in their dissolution of lead, copper or their alloys as opposed to steel. As a result, attempts to remove lead deposit from steel surfaces such as gun barrels lead to undesirable dissolution of a significant portion of the underlying steel surface as well.

Moreover, commercial products marketed for removal of lead or copper fouling from gun barrels generally do not dissolve the lead or copper to be cleaned from the bore, but form an insoluble salt with the lead or copper that must be removed by abrasion, such as with a brass brush.

Accordingly, products and techniques are still needed that allow selective dissolution of the soft metals to allow their easy, nonabrasive removal without serious damage to harder metal substrates.

SUMMARY OF THE INVENTION

Briefly, therefore, the present invention is directed to a novel composition useful for selective dissolution of soft metal such as lead. The composition comprises (1) an organic nitrocompound that, upon exposure to the soft metal, oxidizes the metal to form a first soft metal salt, and (2) a carboxylic acid that, upon exposure to the first said metal salt, reacts with the salt to form a second soft metal salt that is soluble in the composition.

The present invention is also directed to a method for removal of soft metals from harder metal substrates by application to the soft metal of a solvent for the soft metal and removal of the solvent and dissolved metal. The solvent is a composition comprising (1) an organic nitrocompound that, upon exposure to the soft metal oxidizes the metal to form a first soft metal salt, and (2) a carboxylic acid that, upon exposure to the first soft metal salt, reacts with the salt to form a second soft metal salt that is soluble in the composition.

Among the several advantages found to be achieved by the present invention, therefore, may be noted the provision of a composition for dissolution of soft metals such as lead; the provision of such composition that permits removal of the soft metal without substantial abrasion; the provision of such composition that dissolves soft metals selectively to dissolve the soft metal more readily than harder metals in contact with the soft metal; and the provision of a method for removal of soft metal from a harder metal and that has such advantages.

DESCRIPTION OF THE PREFERRED EMBODIMENTS

In accordance with the present invention, it has been discovered that a composition comprising an organic nitrocompound that, upon exposure to a soft metal such as lead, oxidizes the soft metal to form a first soft metal salt, and a carboxylic acid that, upon exposure to the first soft metal salt, reacts with the first soft metal salt to form a second soft metal salt that is soluble in the composition, dissolves soft metals quickly and more readily than harder metals such as steel, thereby allowing the easy removal of soft metal deposits from harder metal surfaces without abrasion and with minimal harm to the underlying harder metal. The composition of the present invention has been found to be extremely aggressive toward soft metals, especially lead, and to a lesser extent copper, tin and cadmium, yet relatively nonaggressive toward harder metals such as steel, nickel and the like.

Ingredients of the composition may be selected with consideration of various preferred advantages with respect to, for example, toxicity to touch or ingestion, smell, explosiveness and so forth.

The organic nitrocompound, as noted, is one that readily oxidizes the soft metal to be dissolved. Nitrobenzene has been found to be particularly suitable in view of its low cost, maintenance of the strong electron withdrawing functionality of the nitro group. For similar reasons, dinitrobenzene, especially p-dinitrobenzene, is also preferred. Moreover, such compositions have other advantages over some other nitro-compounds. For example, trinitro-toluene is a stronger oxidizing agent, but its explosiveness renders it undesirable.

In view of such considerations, preferred nitrocompounds include nitroaromatic compounds, particularly those comprising at least one six-carbon ring, nitroalkanes, especially of from one to about six carbons, salts of such nitroalkanes, nitroalkanols, such as from one to about six carbons, and nitroalkanonitriles, especially those of from two to about six carbons.

Useful nitroaromatic compounds, therefore, include nitrobenzene, 2-, 3-, and 4-nitrotoluene, 2-, 3-, and 4-nitrophenol, 2-, 3-, and 4-chloronitrobenzene, 2-, 3-, and 4-nitroanisole, 2-, 3-, and 4-nitrobenzonitrile, 2-, 3-, and 4-nitrobenzoic acid, 2-, 3- and 4-nitrobenzamide, 2-nitro-m-xylene, 2-nitro-p-xylene, 3-nitro-o-xylene, 1- and 2-nitronaphthalene, 2-nitrobiphenyl and the like. Thus, the aromatic structure may include other pendent substituent groups that retain the oxidizing character of the compound.

Useful nitroalkanes include nitromethane, nitroethane, 1- and 2-nitropropane, 1- and 2-nitro-n-butane, 1- and 2-nitro-n-pentane, 1- and 2-nitro-2-methylpropane, 1- and 2-nitrohexane, and the like. The alkane groups may be substituted groups such as to include minor branches of, for example, alkyl groups of from one to about three carbon atoms. Some of the hydrogens of the alkane groups may be substituted with, for example, halides.

The nitroalkanols may be the alcohols of such compounds; for example, 2-nitroethanol. Useful nitroalkanonitriles include 2-nitroacetonitrile, 4-nitrobutyronitrile and the like.

In any event, however, the particular nitrocompound should have a strong oxidizing functionality sufficient to undergo a redox reaction with the soft metal to form a salt of that metal. The metal to be reduced in particularly preferred cases will be lead or a lead alloy (such as solder, typically an alloy of lead and tin), but may alternatively be copper, cadmium, tin and the like, or an alloy thereof.

The carboxylic acid, then, should be one that, upon exposure to the soft metal salt (e.g., lead salt) produced by the redox reaction between the nitrocompound and the soft metal, reacts with the soft metal salt to form a second soft metal salt that is soluble in the composition containing the nitrocompound and carboxylic acid. By the term "soluble", what is meant is that the salt is at least dispersible in the composition at a high enough concentration such that it may be removed from the underlying surface without mechanical means or use of exorbitant amounts of the composition. This concentration typically is at least about 0.1% by weight, preferably at least about 1% by weight, more preferably at least about 10% by weight total mixture.

Also, the carboxylic acid should not be so aggressive with respect to the underlying hard metal surface that the surface is damaged significantly in the process for removing the soft metal therefrom. Thus, for example, since propionic acid is less aggressive toward steel than is acetic acid, propionic acid may be preferred to acetic acid in many cases.

Odor also may be a significant consideration. For example, butyric acid would be a suitable carboxylic acid, but its strong, disagreeable odor makes it undesirable for use in a solvent.

Monocarboxylic acids particularly useful in this invention may be written as RCOOH, wherein R is an organic radical, especially a alkyl or alkenyl group, wherein one or more of the hydrogens may be substituted with, for example, a halide or a hydroxyl group. In the preferred species, R is a straight chain of six or fewer carbon atoms, but minor branching, such as a methyl or ethyl group is acceptable. Thus, more specifically, preferred saturated carboxylic acids may be written as $X_3C(CX_2)_mCOOH$, wherein the X's are independently —H, —OH or a halide (especially chloride or fluoride) and m is an integer from 0 to about five. More preferably, R is $X_3C(CHX')_mCOOH$, wherein each X is independently halides or —H, most preferably —H, and each X' is independently —H or —OH and m is an integer from 0 to about four. Unsaturated carboxylic acids such as acrylic acid are contemplated as well. Preferably, such unsaturated carboxylic acids have about six or fewer carbon atoms.

Dicarboxylic acids particularly useful in this invention may be written as HOOCR'COOH, wherein R' is an alkylene of from one to about six carbon atoms or an alkenylene group of from two to about six carbon atoms. One or more of the hydrogens in the R' group may be substituted with hydroxyl groups.

Suitable carboxylic acids, therefore, include acetic acid, propionic acid, butyric acid, valeric acid, hexanoic acid, adipic acid, malonic acid, lactic acid, malic acid, tartaric acid, acrylic acid, maleic acid, fumaric acid, chloroacetic acid, trichloroacetic acid, trifluoroacetic acid and the like.

The nitrocompound portion of the composition actually may be made up of a mixture of nitrocompounds as discussed above. Likewise, the carboxylic acid actually may be a mixture of carboxylic acids as discussed above. The nitrocompound and the carboxylic acid may be mixed together in a wide range of molar ratios, such as from 1:100 to 100:1 to form the composition for dissolution of soft metal. Preferably, however, the molar ratio of the nitrocompound to the carboxylic acid in the mixture is in the range of from about 1:10 to about 10:1, more preferably from about 1:1 to about 1:10, even more preferably about 1:2 to about 1:6, and optionally about 1:4.

The composition may also contain an organic solvent. A wide range of organic solvents such as hydrocarbons, alcohols, esters, ethers, chlorinated hydrocarbons, mixtures of such solvents, and the like may be used. For example, pentane, hexane, octane, gasoline, kerosene, diesel oil, methanol, ethanol, isopropanol, butanol, ethyl acetate, methyl butyrate, diethyl ether, methylisobutyl ether, diphenyl ether, dichloromethane, trichloroethylene, trichloro ethane, acetone, methylisobutyl ketone, dimethylformamide, acetonitrile, dimethylsulfoxide, tetrahydrofuran, cyclohexane, mineral oil, ethylene glycol monobutyl ether (butyl Cellosolve), and the like may be employed. Petroleum distillates have been found to be particularly useful.

The organic solvent may be added to the composition to serve any one or more of several purposes. If the nitrocompound or carboxylic acid is not liquid or is overly viscous, then the organic solvent may be used to dissolve the nitrocompound to form a liquid composition or to reduce the viscosity. The organic solvent may also—or alternatively—be used as a solvent for the second soft metal salt formed by the reaction of the carboxylic acid with the salt formed by the reaction between the nitrocompound and the soft metal. Or, the organic solvent may be used as a diluent for the more expensive components.

Other components may be included as well. For example, an oil may be added to the composition to protect the harder metal substrate from corrosion after the nitrocompound and carboxylic acid evaporate. A substance such as butyl propionate may be incorporated into the composition to improve the smell. Still other components may be included for other desirable properties. The composition, however, should be nonaqueous, although minor quantities of water might be present under some circumstances, typically as a result of hydration or impurity. Thus, the composition is nonaqueous recognizing, however, that such minor quantities of water might be present under some circumstances.

The nitrocompound and carboxylic acid combined, therefore, make up about 1 percent to 100 percent of the weight of the total composition. Preferably, the nitrocompound and the carboxylic acid should make up from about 5 percent to 100 percent of the total composition. If the nitrocompound and carboxylic acid make up less than 100 percent of the composition, the bulk of the remainder of the composition is preferably made up of the organic solvent or mixtures of solvents.

In application, the composition may be brought into contact with a soft metal and allowed to remain in contact for a time sufficient for the soft metal to dissolve. Although the composition of this invention has been found to be selectively more aggressive toward softer metals, it may still exhibit some, although lesser, aggressiveness toward harder metals. Thus, if the soft metal is being removed from a harder metal surface, the composition should be removed before unacceptable damage to the harder metal occurs. Soft metals for which the composition is especially effective (and likewise, a composition of desirable effectiveness for dissolution of a particular soft metal such as lead) may be determined by a test according to which the tested metal is added to the composition. For the particular desired combination of composition and soft metal, one gram of the composition at 25° C. can dissolve at least about 0.01 grams of the metal from a one square centimeter of metal surface in 24 hours.

In the case in which the fouled barrel of a gun, such as a rifle, is to be cleaned, the barrel may be swabbed with a cloth patch wetted with the composition. The barrel is then allowed to stand for a few minutes, after which it is swabbed with a dry cloth to remove the composition and dissolved lead, tin or copper. Although other metals such as antimony that may be present minor amounts in an alloy being treated may not dissolve in the composition, the simple dissolution of the major component of the alloy reduces the metals such as antimony to a fine powder. That powder then is often suspended in the cleaning composition, permitting easy removal by wiping with a cloth.

Badly fouled barrels may be filled with the composition and allowed to stand for an hour or more. The barrel then may be emptied, swabbed with a dry cloth and oiled for protection from corrosion.

It has been found that the composition dissolves lead much faster than copper and copper much faster than steel. Because the rate of dissolution of lead is much greater than that of copper, the composition also may be used to remove solder from electrical connections. For example, the composition of this invention may be used to dissolve the solder from the copper parts of automobile starters and generators, allowing recovery of the solder for salvage without dissolving much of the copper.

The following examples describe preferred embodiments of the invention. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples. In the examples all percentages are given on a weight basis unless otherwise indicated.

EXAMPLE 1

A sample composition was prepared by mixing together nitrobenzene (7.5 gm), acetic acid (50 ml) and acetic anhydride (50 ml). The mixture was charged with lead to a reactor jacketed with cooling water to maintain the temperature of the reacting mixture between 24° and 30° C. The lead (20.5 gm, 99+% pure) was added periodically in small quantities (1 to 3 gm each). After all the lead (20.7 gm) dissolved, the solution was analyzed by gas chromatography. All of the lead and about 75% of the nitrobenzene were found to have reacted.

EXAMPLE 2

The procedure of Example 1 was followed with cadmium (11.2 gm) in place of lead. No exotherm was noted at room temperature, so the reaction temperature was increased to 80° C. After six hours, the solution was analyzed. It was found that about 28% of the cadmium and about 17% of the nitrobenzene reacted.

EXAMPLE 3

The procedure of Example 1 was followed with tin (11.9 gm) in place of lead. The reaction seemed to be progressing slowly at room temperature, so the reaction temperature was increased to 99° C. An off-white precipitate formed and so the reactor was disassembled to recover the solution. The solid was filtered and discarded. The filtrate was analyzed and unreacted tin metal was recovered from the reactor. It was found that about 60% of the tin and about 61% of the nitrobenzene reacted.

EXAMPLE 4

The procedure of Example 1 was followed with aluminum (2.7 gm) in place of lead. No reaction was indicated by apparent dissolution or by gas chromatography.

EXAMPLE 5

Another sample composition was prepared by mixing together propionic acid (15 ml), nitrobenzene (15 ml), mineral oil (15 ml), kerosene (15 ml), butyl propionate (5 ml) and butyl Cellosolve (35 ml). The composition had an odor that was deemed non-offensive. The lead and copper dissolving efficacy of the resulting composition was tested against those of a variety of commercial products by placing foil of the tested metal (lead in one trial and copper in another) in a sample (3 ml) of the tested product and weighing the metal foil periodically. The weight loss of the foil was viewed as indicative of the amount of the metal that dissolved. The results were as follows, with the composition prepared according to the method set forth above in this Example as "Composition 2":

| Lead Dissolution: | | | | | |
| --- | --- | --- | --- | --- | --- |
| WEIGHT OF LEAD FOIL (GRAMS) | | | | | |
| | Number of Days After Insertion of Foil | | | | |
| LEAD SOLVENT | 0 | 1 | 7 | 15 | 35 |
| Sweet's 7.62 Solvent | 0.24 | 0.235 | 0.235 | 0.235 | 0.23 |
| Proshot Solvent II | 0.23 | 0.21 | 0.21 | 0.2 | 0.18 |
| Hoppe's #9 | 0.22 | 0.2 | 0.195 | 0.185 | 0.155 |
| Shooter's Choice | 0.27 | 0.255 | 0.245 | 0.235 | 0.21 |
| Accubore | 0.32 | 0.295 | 0.28 | 0.265 | 0.23 |
| Shiloh Creek | 0.345 | | | 0.345 | 0.345 |
| Composition 2 | 0.3 | 0 | | | |

Copper Dissolution:

WEIGHT OF COPPER FOIL (GRAMS)

| COPPER SOLVENT | Number of Days After Insertion of Foil | | | | |
| --- | --- | --- | --- | --- | --- |
|  | 0 | 1 | 7 | 15 | 35 |
| Sweet's 7.62 Solvent | 0.175 | 0.17 | 0.16 | 0.145 | 0.12 |
| Proshot Solvent II | 0.145 | 0.145 | 0.14 | 0.14 | 0.12 |
| Hoppe's #9 | 0.18 | 0.18 | 0.18 | 0.175 | 0.165 |
| Shooter's Choice | 0.12 | 0.115 | 0.115 | 0.105 | 0.095 |
| Accubore | 0.175 | 0.17 | 0.17 | 0.165 | 0.165 |
| Shiloh Creek | 0.19 |  |  | 0.19 | 0.19 |
| Composition 2 | 0.17 | 0.165 | 0.165 | 0.16 | 0.15 |

In view of the above, it will be seen that the several advantages of the invention are achieved and other advantageous results attained.

As various changes could be made in the above methods and compositions without departing from the scope of the invention, it is intended that all matter contained in the above description and shown in the accompanying drawings shall be interpreted as illustrative and not in a limiting sense.

What is claimed:

1. A method for selectively dissolving a soft metal from a substrate of a harder metal, comprising:

contacting the soft metal with a nonaqueous liquid composition that reacts with the soft metal selectively versus the harder metal to form a soft metal salt of a carboxylic acid soluble in the nonaqueous liquid composition;

maintaining contact between the nonaqueous liquid composition and the soft metal for a time sufficient to form the soft metal salt of the carboxylic acid; and removing from the harder metal the nonaqueous liquid composition along with at least a portion of the soft metal salt of the carboxylic acid thereby to expose at least a portion of the harder metal of the substrate;

the nonaqueous liquid composition comprising:

an organic nitrocompound that, upon exposure to the soft metal, oxidizes the soft metal to form a first soft metal salt; and a carboxylic acid that, upon exposure to the soft metal salt, reacts with the first soft metal salt to form the soft metal salt of the carboxylic acid.

2. A method as set forth in claim 1 wherein the organic nitrocompound is selected from the group consisting of nitroaromatic compounds comprising at least one six-carbon ring, nitroalkanes of from one to about six carbons, nitroalkanols of from one to about six carbons and nitroalkanonitriles of from two to about six carbons.

3. A method as set forth in claim 2 wherein the organic nitrocompound is selected from the group consisting of nitrobenzene, nitrotoluene, nitrophenol, chloronitrobenzene, nitroanisole, hexylnitrobenzene, nitrobenzonitrile, nitrobenzoic acid, nitrobenzamide, nitroxylene, nitronaphthalene and nitrobiphenyl.

4. A method as set forth in claim 3 wherein the soft metal is selected from the group consisting of lead, copper, cadmium, tin and alloys thereof, and the harder metal is selected from the group consisting of steel, stainless steel and nickel.

5. A method as set forth in claim 3 wherein the soft metal is solder and the harder metal is copper.

6. A method as set forth in claim 3 wherein the liquid composition further comprises an organic solvent.

7. A method as set forth in claim 2 wherein the organic nitrocompound is nitrobenzene.

8. A method as set forth in claim 7 wherein the soft metal is lead.

9. A method as set forth in claim 7 wherein the soft metal is selected from the group consisting of lead, copper, cadmium, tin and alloys thereof, and the harder metal is selected from the group consisting of steel, stainless steel and nickel.

10. A method as set forth in claim 9 wherein the soft metal is lead.

11. A method as set forth in claim 2 wherein the soft metal is selected from the group consisting of lead, copper, cadmium, tin and alloys thereof, and the harder metal is selected from the group consisting of steel, stainless steel and nickel.

12. A method as set forth in claim 1 wherein the carboxylic acid is selected from the group consisting of acetic acid, propionic acid, butyric acid, lactic acid, and mixtures thereof.

13. A method as set forth in claim 1 wherein the nitrocompound and carboxylic acid are dissolved in a solvent selected from the group consisting of kerosene, toluene, mineral oil, glycol ethers, acetone, methyl ethyl ketone, methanol, isoproponal, ethyl acetate, acetonitrile and mixtures thereof.

14. A method as set forth in claim 13 wherein the liquid composition further comprises an odorous compound.

15. A method as set forth in claim 1 wherein the substrate is a steel gun for a rifle barrel which has deposited thereon lead, lead alloys, copper or a mixture thereof.

16. A method as set forth in claim 1 wherein the liquid composition is sufficiently aggressive toward a surface of lead that a one gram sample of the liquid composition at 25° C., upon exposure to one square centimeter of the surface of lead for 24 hours, dissolves at least about 0.01 grams of the surface of lead.

17. A method as set forth in claim 1 wherein the soft metal is selected from the group consisting of lead, copper, cadmium, tin and alloys thereof, and the harder metal is selected from the group consisting of steel, stainless steel and nickel.

18. A method as set forth in claim 17 wherein the carboxylic acid is selected from the group consisting of acetic acid, propionic acid, butyric acid, lactic acid and mixtures thereof.

19. A method as set forth in claim 17 wherein the nitrocompound and carboxylic acid are dissolved in a solvent selected from the group consisting of kerosene, toluene, mineral oil, glycol ethers, acetone, methyl ethyl ketone, methanol, isopropanol, ethyl acetate, acetonitrile and mixtures thereof.

20. A method as set forth in claim 1 wherein the soft metal is lead or a lead alloy and the harder metal is copper.

21. A method as set forth in claim 20 wherein the soft metal is solder.

22. A method as set forth in claim 1 wherein the liquid composition further comprises an organic solvent.

23. A method for selectively dissolving a soft metal from a substrate of a harder metal, comprising:

contacting the soft metal with a liquid composition that reacts with the soft metal selectively versus the harder metal to form a soft metal salt of a carboxylic acid soluble in the liquid composition;

maintaining contact between the liquid composition and the soft metal for a time sufficient to form the soft metal salt of the carboxylic acid; and removing from the harder metal the liquid composition along with at least a portion of the soft metal salt of the carboxylic acid thereby to expose at least a portion of the harder metal of the substrate, the liquid composition consisting essentially of nonaqueous components, including:

an organic nitrocompound that, upon exposure to the soft metal, oxidizes the soft metal to form a first soft metal salt;

a carboxylic acid that, upon exposure to the soft metal salt, reacts with the first soft metal salt to form the soft metal salt of the carboxylic acid; and an organic solvent.

24. A method as set forth in claim 23 wherein the organic nitrocompound is selected from the group consisting of nitroaromatic compounds comprising at least one six-carbon ring, nitroalkanes of from one to about six carbons, nitroalkanols of from one to about six carbons and nitroalkanonitriles of from two to about six carbons.

25. A method as set forth in claim 24 wherein the soft metal is selected from the group consisting of lead, copper, cadmium, tin and alloys thereof, and the harder metal is selected from the group consisting of steel, stainless steel and nickel.

26. A method as set forth in claim 23 wherein the soft metal is selected from the group consisting of lead, copper, cadmium, tin and alloys thereof, and the harder metal is selected from the group consisting of steel, stainless steel and nickel.

27. A method as set forth in claim 23, wherein the organic solvent is selected from the group consisting of kerosene, toluene, mineral oil, glycol ethers, acetone, methyl ethyl ketone, methanol, isopropanol, ethyl acetate, acetonitrile, and mixtures thereof.

28. A method as set forth in claim 23 wherein the soft metal is lead or a lead alloy and the harder metal is copper.

* * * * *